(12) United States Patent
Yamamoto

(10) Patent No.: US 8,586,065 B2
(45) Date of Patent: Nov. 19, 2013

(54) OIL-IN-WATER EMULSIFIED COSMETIC COMPOSITION

(75) Inventor: Yumiko Yamamoto, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/858,389

(22) Filed: Aug. 17, 2010

(65) Prior Publication Data

US 2010/0311836 A1    Dec. 9, 2010

Related U.S. Application Data

(62) Division of application No. 10/863,498, filed on Jun. 9, 2004, now abandoned.

(30) Foreign Application Priority Data

Jun. 10, 2003 (JP) .................................. 2003-165804

(51) Int. Cl.
*A61K 8/06* (2006.01)
*A61K 8/41* (2006.01)
*A61K 8/42* (2006.01)

(52) U.S. Cl.
USPC ........... 424/401; 564/192; 564/224; 564/506; 564/507; 564/508

(58) Field of Classification Search
None
See application file for complete search history.

(56) References Cited

U.S. PATENT DOCUMENTS

| 5,304,334 | A | 4/1994 | Lahanas et al. |
| 5,627,056 | A | 5/1997 | Casey et al. |
| 5,922,764 | A * | 7/1999 | Cantin et al. .................. 514/557 |
| 2002/0022611 | A1 * | 2/2002 | Fujimura et al. ......... 514/210.01 |
| 2003/0215414 | A1 | 11/2003 | Lambers |
| 2004/0018218 | A1 | 1/2004 | Philippe et al. |

FOREIGN PATENT DOCUMENTS

| EP | 227994 | * 8/1987 | ............ C07C 103/38 |
| JP | 08-056569 | 3/1996 | |
| JP | 8-109121 | 4/1996 | |
| JP | 2000-191496 | 7/2000 | |
| JP | 2001 13199872 | 7/2001 | |
| JP | 2002-114631 | 4/2002 | |
| JP | 2002-212100 | 7/2002 | |
| WO | WO 03/049709 | 6/2003 | |

OTHER PUBLICATIONS

Machine translation of JP 08-056569 (1996).*
Machine translation of JP 2002-114631 (2002).*
Patent Abstracts of Japan, JP 2001-099872, Apr. 13, 2001.

* cited by examiner

*Primary Examiner* — Daniel Sullivan
*Assistant Examiner* — Barbara Frazier
(74) *Attorney, Agent, or Firm* — Oblon, Spivak, McClelland, Maier & Neustadt, L.L.P.

(57) ABSTRACT

The present invention relates to an oil-in-water emulsified cosmetic composition, which contains an emulsion having (A) a sphingosine represented by formula (1), (B) an acid compound selected from inorganic acids and organic acids having 5 or less carbon atoms, and (C) a ceramide represented by formula (2); and another emulsion having (D) an oil component selected from polar oils and hydrocarbon oils, and (E) a surfactant. The oil-in-water emulsified cosmetic composition contains a ceramide and is excellent in emulsion stability.

17 Claims, No Drawings

OIL-IN-WATER EMULSIFIED COSMETIC COMPOSITION

FIELD OF THE INVENTION

The present invention relates to an oil-in-water emulsified cosmetic composition containing a ceramide-containing oil component.

BACKGROUND OF THE INVENTION

The stratum corneum, the outermost layer of skin, prevents ingress of harmful substances into the skin and moisture loss from the skin and at the same time, has a function of keeping flexibility or smooth appearance of the skin by retaining water in itself. Lipids called horny intercellular lipids (which will hereinafter be called "horny ICL") exist so as to fill the interstices between numerous corneocytes.

In this horny ICL, almost 50% of the lipids are ceramides, and there are also cholesterol, cholesterol esters, fatty acids and the like. It is generally known that a decrease of horny ICL, especially of ceramides, triggers detrimental conditions in the skin, such as rough skin, dry skin or aged skin. The stratum corneum having a deteriorated function can be improved by the external use of ceramide as a component for improving the function of the stratum corneum.

Nonetheless, it is difficult to maintain the stability of a ceramide in a formulation, because it tends to crystallize readily and has a high melting point. When a ceramide is used in combination with another oil component, more than one surfactant is required depending on the differences of emulsifying activities thereof and in addition, the amount of the surfactants to be added tends to increase.

In Japanese Patent Application Laid-Open No. Hei 8-109121, described is a process of using an oil agent having good compatibility with a ceramide for the purpose of forming a stable composition of a ceramide without using a surfactant. This process is, however, not adequate for imparting a variety of functions and does not result in an adequate good skin feeling composition, because the oil agent to be used in combination is limited to those having good compatibility with a ceramide.

An oil-in-water emulsified cosmetic composition, on the other hand, has water as a continuous phase, so that it provides a light feeling and in addition, is refreshing to the eyes and to the touch. When a mixture of a ceramide with the other oil component is emulsified, such an oil-in-water emulsified cosmetic composition tends to worsen the feeling upon use and the emulsion itself becomes less stable.

SUMMARY OF THE INVENTION

In the present invention, there is provided an oil-in-water emulsified cosmetic composition containing an emulsion containing (A) a sphingosine represented by the following formula (1):

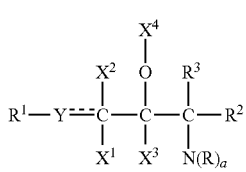

(1)

(wherein, $R^1$ represents a linear, branched or cyclic, saturated or unsaturated $C_{4-30}$ hydrocarbon group which may be substituted by a hydroxyl, carbonyl or amino group; Y represents a methylene group, a methine group or an oxygen atom; $X^1$, $X^2$ and $X^3$ each independently represent a hydrogen atom, a hydroxyl group or an acetoxy group, $X^4$ represents a hydrogen atom, an acetyl group or a glyceryl group or forms an oxo group together with the adjacent oxygen atom (with the proviso that when Y represents a methine group, either $X^1$ or $X^2$ represents a hydrogen atom and the other one does not exist and when $X^4$ forms an oxo group, $X^3$ does not exist); $R^2$ and $R^3$ each independently represent a hydrogen atom, a hydroxyl group, a hydroxymethyl group or an acetoxymethyl group; R each independently represents a hydrogen atom or an amidino group, or a linear or branched, saturated or unsaturated hydrocarbon group having 1 to 8 carbon atoms in total and optionally having a substituent selected from hydroxyl, hydroxyalkoxy, alkoxy and acetoxy groups; a stands for 2 or 3; and a dashed line indicates a saturated bond or unsaturated bond), (B) an acid compound selected from inorganic acids and organic acids having carbon atoms of 5 or less, and (c) a ceramide represented by the following formula (2):

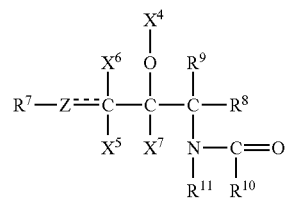

(2)

(wherein, $R^7$ represents a linear, branched or cyclic, saturated or unsaturated $C_{4-30}$ hydrocarbon group which may be substituted by a hydroxyl, carbonyl or amino group, or a hydrogen atom; Z represents a methylene group, a methine group or an oxygen atom; $X^5$, $X^6$ and $X^7$ each independently represent a hydrogen atom, a hydroxyl group or an acetoxy group, $X^4$ represents a hydrogen atom, an acetyl group or a glyceryl group or forms an oxo group together with the adjacent oxygen atom (with the proviso that when Z represents a methine group, either $X^5$ or $X^6$ represents a hydrogen atom and the other one does not exist and when $X^4$ forms an oxo group, $X^7$ does not exist); $R^8$ and $R^9$ each independently represent a hydrogen atom, a hydroxyl group, a hydroxymethyl group or an acetoxymethyl group; $R^{10}$ represents a linear, branched or cyclic, saturated or unsaturated $C_{5-60}$ hydrocarbon group which may be substituted by a hydroxyl, carbonyl or amino group and may have an ether bond, ester bond or amide bond in the main chain; $R^{11}$ represents a hydrogen atom, or a linear or branched, saturated or unsaturated hydrocarbon group having 1 to 30 carbon atoms in total and optionally having a substituent selected from hydroxyl, hydroxyalkoxy, alkoxy and acetoxy groups (with the proviso that when $R^7$ represents a hydrogen atom and Z represents an oxygen atom, $R^{11}$ represents a hydrocarbon group having 10 to 30 carbon atoms in total and when $R^7$ represents a hydrocarbon group, $R^{11}$ represents a hydrocarbon group having 1 to 8 carbon atoms in total); and a dashed line indicates a saturated bond or unsaturated bond), and another emulsion containing (D) an oil component selected from polar oils and hydrocarbon oils and (E) a surfactant.

In another aspect of the present invention, there is also provided a preparation process of the above-described oil-in-water emulsified cosmetic composition, which includes the steps of mixing an emulsion obtained by emulsifying (C) a ceramide represented by formula (2) with (A) a sphingosine represented by formula (1) and (B) an acid compound selected from inorganic acids and organic acids having 5 or less carbon atoms, and another emulsion obtained by emulsifying (D) an oil component selected from polar oils and hydrocarbon oils with (E) a surfactant.

DETAILED DESCRIPTION OF THE INVENTION

The present invention relates to an oil-in-water emulsified cosmetic composition containing a ceramide-containing oil component and having excellent emulsion stability.

Upon emulsification of oil components including a ceramide represented by formula (2), preferably mixing them after emulsification of the ceramide and the other oil components separately makes it possible to prepare an oil-in-water emulsified cosmetic composition having an excellent emulsion stability without impairing the emulsified state of the ceramide.

In general, although not wanting to be limited by theory, a ceramide is a substance that is easy to crystallize but hard to emulsify, and therefore, the kinds of surfactant that can be used as an emulsifier are limited. In addition, when a ceramide is emulsified as a mixture with the other oil component for cosmetics, this mixture leads to a dissolved state depending on the type of the oil component or surfactant used. It therefore becomes difficult to keep the stability of the emulsion system. To maintain the emulsified state of the ceramide, the amount of a surfactant inevitably increases.

When a ceramide is emulsified using a sphingosine and an acid compound, on the other hand, the emulsified state of the ceramide is presumed to be stable, because they form a liquid crystal structure and crystallization of the ceramide is suppressed. Once the emulsion of the ceramide obtained by emulsification with a sphingosine becomes stable, the emulsion system tends to strengthen against any damage even when mixed with an oil component or another component which may inhibit emulsion stability of the ceramide. Therefore, it is possible not only to attain a stable emulsion but also to simplify the emulsifying process by which a ceramide and another oil component are individually emulsified and then mixed with each other.

Moreover, use of a salt of a sphingosine as an emulsifier of a ceramide contributes to a reduction in the amount of surfactant to be used for the whole cosmetic composition, whereby the composition has an excellent feeling upon use.

The sphingosine usable as Component (A) in the present invention is represented by the above-described formula (1).

In the formula, $R^1$ represents a linear, branched or cyclic, saturated or unsaturated $C_{4-30}$ hydrocarbon group which may be substituted by a hydroxyl, carbonyl or amino group, preferably a linear, branched or cyclic, saturated or unsaturated $C_{7-22}$ hydrocarbon group which may be substituted by a hydroxyl group. More preferably, $R^1$ is a linear or branched $C_{10-20}$ alkyl group or a linear or branched $C_{10-20}$ alkyl group having, at a terminal thereof on the Y side, a hydroxyl group. When it is a branched alkyl group, it preferably has a methyl branched alkyl chain. More preferred examples include tridecyl, tetradecyl, pentadecyl, hexadecyl, 1-hydroxytridecyl, 1-hydroxypentadecyl, isohexadecyl and isostearyl groups.

Y represents any one of a methylene group ($CH_2$), a methine group (CH) and an oxygen atom.

$X^1$, $X^2$ and $X^3$ each independently represent a hydrogen atom, a hydroxyl group or an acetoxy group, $X^4$ represents a hydrogen atom, an acetyl group, a glyceryl group or a substituent forming an oxo group together with the adjacent oxygen atom. Of these, preferred is the case where at most one of $X^1$, $X^2$ and $X^3$ represents a hydroxyl group, the remaining ones represent a hydrogen atom, and $X^4$ represents a hydrogen atom. When Y represents a methine group, either $X^1$ or $X^2$ represents a hydrogen atom and the other one does not exist. When $X^4$ forms an oxo group, $X^3$ does not exist.

$R^2$ and $R^3$ each independently represent a hydrogen atom, a hydroxyl group, a hydroxymethyl group or an acetoxymethyl group. $R^3$ is preferably a hydrogen atom.

The letter "a" stands for 2 or 3. When a stands for 2, R means $R^4$ or $R^5$ and when a stands for 3, R means $R^4$, $R^5$ or $R^6$.

$R^4$, $R^5$ and $R^6$ each independently represent a hydrogen atom or an amidino group, or a linear or branched, saturated or unsaturated hydrocarbon group having 1 to 8 carbon atoms in total and optionally having a substituent selected from hydroxyl, hydroxyalkoxy, alkoxy and acetoxy groups. As the hydroxyalkoxy group which may be a substituent for the hydrocarbon group, linear or branched $C_{1-7}$ hydroxyalkoxy groups are preferred. As the alkoxy group, linear or branched $C_{1-7}$ alkoxy groups are preferred. Examples of $R^4$, $R^5$ or $R^6$ include a hydrogen atom; linear or branched alkyl groups such as methyl, ethyl, propyl, 2-ethylhexyl and isopropyl; alkenyl groups such as vinyl and allyl; amidino groups; and hydrocarbon groups having 1 to 8 carbon atoms in total and having 1 to 6 substituents selected from hydroxyl group, hydroxyalkoxy group and alkoxy groups, such as hydroxymethyl, 2-hydroxyethyl, 1,1-dimethyl-2-hydroxyethyl, 2-hydroxypropyl, 2,3-dihydroxypropyl, 2-hydroxy-3-methoxypropyl, 2,3,4,5,6-pentahydroxyhexyl, 1,1-bis(hydroxymethyl)ethyl, 2-(2-hydroxyethoxy)ethyl, 2-methoxyethyl, 1-methyl-2-hydroxyethyl, 3-hydroxypropyl, 3-methoxypropyl, and 1,1-bis(hydroxymethyl)-2-hydroxyethyl.

Of these, a hydrogen atom, a methyl group, and an alkyl group which may be substituted by 1 to 3 substituents selected from hydroxyl group and hydroxyalkoxy groups, such as 2-hydroxyethyl, 1,1-dimethyl-2-hydroxyethyl, 1,1-bis(hydroxymethyl)ethyl, 2-(2-hydroxyethoxy)ethyl are more preferred.

As the sphingosine represented by formula (1), a natural or natural type sphingosine, or derivative thereof represented by the below-described formula (3) (which will hereinafter be described as "natural type sphingosine", collectively), or a pseudo type sphingosine having a sphingosine structure represented by formula (4) (which will hereinafter be described as "pseudo type sphingosine") is preferred.

(I) Natural type sphingosine represented by formula (3):

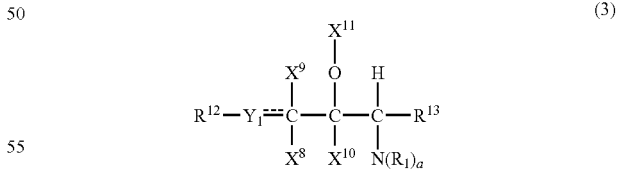

(wherein, $R^{12}$ represents a linear, branched or cyclic, saturated or unsaturated $C_{7-19}$ hydrocarbon group which may be substituted by a hydroxyl group; $Y_1$ represents a methylene or methine group; $X^8$, $X^9$ and $X^{10}$ each independently represent a hydrogen atom, a hydroxy group or an acetoxy group, $X^{11}$ represents a hydrogen atom or forms an oxo group together with the adjacent oxygen atom (with the proviso that when $Y_1$ represents a methine group, either $X^8$ or $X^9$ represents a hydrogen atom and the other one does not exist, and when $X^{11}$ forms an oxo group, $X^{10}$ does not exist); $R^{13}$ represents a hydroxymethyl or acetoxymethyl group; $R_1$ each independently represents a hydrogen atom or an amidino group, or a linear or branched, saturated or unsaturated hydrocarbon group having 1 to 4 carbon atoms in total and optionally having a substituent selected from hydroxyl, hydroxyalkoxy, alkoxy and acetoxy groups; a stands for 2 or 3; and a dashed line indicates a saturated bond or unsaturated bond).

As $R^{12}$, linear, branched or cyclic, saturated or unsaturated $C_{7-19}$ hydrocarbon groups are preferred, with linear, saturated or unsaturated $C_{13-15}$ hydrocarbon groups being more preferred. It is preferred that a stands for 2 and $R_1$s each independently represent a hydrogen atom or a linear or branched $C_{1-4}$ alkyl group.

Specific examples of the natural type sphingosine represented by formula (3) include natural sphingosine, dihydrosphingosine, phytosphingosine, sphingadienine, dehydrosphingosine, and dehydrophytosphingosine and N-alkyl derivatives (e.g., N-methyl derivatives) thereof.

As these sphingosines, natural (D(+) form) optically active derivatives, unnatural (L(−) form) optically active derivatives or a mixture thereof may be used. The relative configuration of these compounds may be any one of the configuration of a natural form, that of an unnatural form and that of their mixture.

Moreover, PHYTOSPHINGOSINE (listed in INCI; 8th Edition) and those represented by the below-described formulas are preferred.

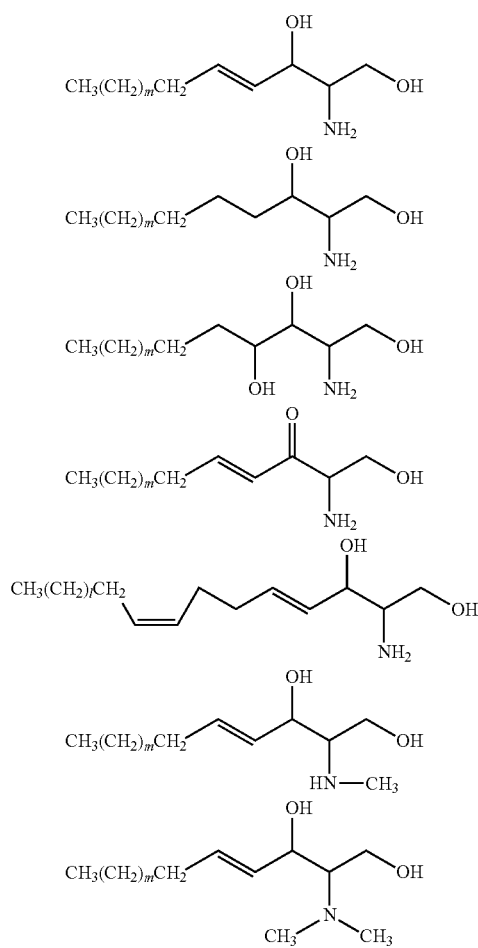

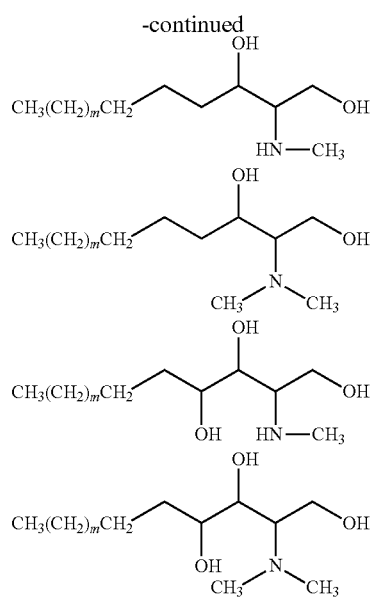

(wherein, m stands for 5 to 17 and l stands for 1 to 13).

They may be an extract from natural sphingosine or a synthesized product thereof. A commercially available one can also be used.

Examples of the commercially available natural type sphingosine include D-Sphingosine (4-Sphingenine) (product of SIGMA-ALDRICH), DS-phytosphingosine (product of DOOSAN) and phytosphingosine (product of Cosmo Ferm).

(II) Pseudo type sphingosines represented by the following formula (4)

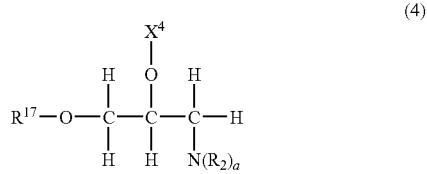

(4)

(wherein, $R^{17}$ represents a linear, branched or cyclic, saturated or unsaturated $C_{10-22}$ hydrocarbon group which may be substituted by a hydroxyl group; $X^4$ represents a hydrogen atom, an acetyl group or a glyceryl group; $R_2$ each independently represents a hydrogen atom or an amidino group, or a linear or branched, saturated or unsaturated hydrocarbon group having 1 to 8 carbon atoms in total and optionally having a substituent selected from hydroxyl, hydroxyalkoxy, alkoxy and acetoxy groups, and a stands for 2 or 3).

As $R^{17}$, iso-branched alkyl groups having 14 to 20 carbon atoms are preferred, with an isostearyl group being more preferred. Still more preferred is an isostearyl group available by using as a raw material oil an isostearyl alcohol derived from a by-product of dimer acid preparation using a fatty acid derived from an animal or plant oil.

When a stands for 2, $R_2$ means $R^{18}$ or $R^{19}$, while when a stands for 3, $R_2$ means $R^{18}$, $R^{19}$ or $R^{20}$.

Examples of $R^{18}$, $R^{19}$ or $R^{20}$ include a hydrogen atom; linear or branched alkyl groups such as methyl, ethyl, propyl, 2-ethylhexyl and isopropyl; alkenyl groups such as vinyl and allyl; an amidino group; and alkyl groups having 1 to 8 carbon atoms in total and having a substituent selected from hydroxyl, hydroxyalkoxy and alkoxy groups, such as hydroxymethyl, 2-hydroxyethyl, 1,1-dimethyl-2-hydroxyethyl, 2-hydroxypropyl, 2,3-dihydroxypropyl, 2-hydroxy-3-methoxypropyl, 2,3,4,5,6-pentahydroxyhexyl, 1,1-bis(hydroxymethyl)ethyl, 2-(2-hydroxyethoxy)ethyl, 2-methoxyethyl, 1-methyl-2-hydroxyethyl, 3-hydroxypropyl, 3-methoxypropyl, and 1,1-bis(hydroxymethyl)-2-hydroxyethyl.

A secondary amine having as either $R^{18}$ or $R^{19}$ a hydrogen atom and as the other one a 2-hydroxyethyl, 1,1-dimethyl-2-hydroxyethyl, 1,1-bis(hydroxymethyl)ethyl or 2-(2-hydroxyethoxy)ethyl group is still more preferred.

As the pseudo type sphingosine, that having as $R^{17}$ an isostearyl group, as $X^4$ a hydrogen atom, as $R^{18}$ a hydrogen atom, and as $R^{19}$ an alkyl group having 1 to 3 substituents selected from hydroxyl and hydroxyalkoxy groups, such as 2-hydroxyethyl, 1,1-bis(hydroxymethyl)ethyl, 1,1-dimethyl-2-hydroxyethyl or 2-(2-hydroxyethoxy)ethyl group is preferred.

The following pseudo type sphingosines (i) to (iv) are specific examples of the pseudo type sphingosine.

ton nuclear magnetic resonance spectroscopy which has conventionally been used for identification of the structure of a compound.

As Component (B), the acid compound having a pH of 1 or greater but less than 7 as measured at 25° C. using its 0.1 mol/L aqueous solution is preferred, with that having a pH of from 1 to 6.5 being more preferred.

Examples of the inorganic acid include phosphoric acid, hydrochloric acid, nitric acid, sulfuric acid, perchloric acid and carbonic acid, with phosphoric acid and hydrochloric acid being preferred.

Examples of the organic acid include monocarboxylic acids such as formic acid, acetic acid, propionic acid, butyric acid, isobutyric acid, and valeric acid; dicarboxylic acids such as succinic acid, phthalic acid, fumaric acid, oxalic acid, malonic acid and glutaric acid; oxycarboxylic acids such as glycolic acid, citric acid, lactic acid, pyruvic acid, malic acid and tartaric acid; and amino acids such as glutamic acid and aspartic acid.

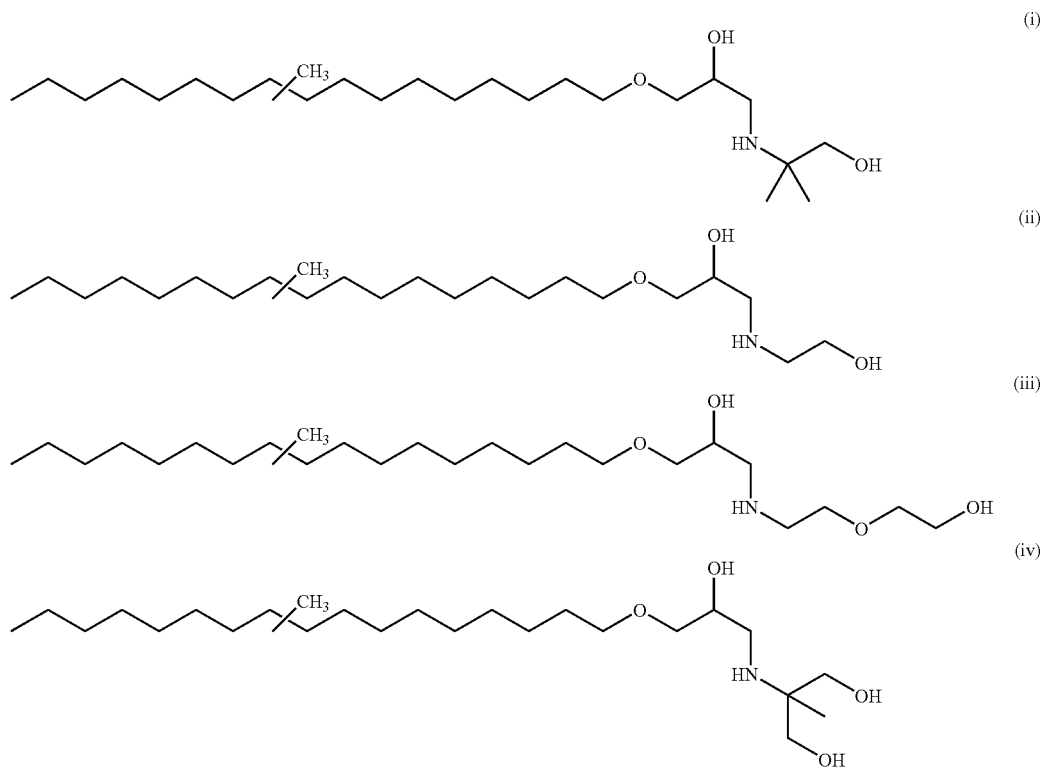

As Component (A), two or more compounds may be used in combination. The content of Component (A) in the cosmetic composition of the present invention is preferably from 0.001 to 10 weight %, more preferably from 0.005 to 3 weight %, still more preferably from 0.01 to 1.5 weight %.

The acid compound (B) of the present invention selected from inorganic acids and organic acids having 5 or less carbon atoms is considered to form its salt with the amine group of the sphingosine (A) by acid-base neutralization and the sphingosine cationized by this reaction acquires a function as an activator. The state of the salt of the sphingosine can be determined by an infrared absorption spectroscopy or a pro- Of these, phosphoric acid, hydrochloric acid, succinic acid, citric acid, lactic acid, glutamic acid and aspartic acid are preferred, with lactic acid, glutamic acid and aspartic acid being more preferred.

As Component (B), two or more compounds may be used in combination. The content of Component (B) in the cosmetic composition of the present invention is preferably from 0.001 to 10 weight %, more preferably from 0.005 to 3 weight %, still more preferably from 0.01 to 1.5 weight %.

Component (B) is preferably added in an amount of at least 0.3 mole, preferably 0.3 to 5 moles, more preferably 0.5 to 3 moles, per mole of Component (A) in order to cationize the amine of the sphingosine (A). For example, it is preferred that an aqueous solution of Component (B) mixed with an equimolar amount of Component (A) have a pH of from 2 to 6 at 25° C. (as measured by "HORIBA pH METER F-22" after correction with a phthalate standard solution). The cationized sphingosine salt which has acquired an activator-like function is considered to suppress crystallization of a ceramide having a close relationship with the hydrophobic moiety of the sphingosine and forms a stable emulsified condition.

The ceramide which is Component (C) in the present invention is represented by the above-described formula (2).

In the formula, $R^7$ represents a linear, branched or cyclic, saturated or unsaturated $C_{4-30}$ hydrocarbon group which may be substituted by a hydroxyl, carbonyl or amino group, preferably a linear, branched or cyclic, saturated or unsaturated $C_{7-22}$ hydrocarbon group which may be substituted by a hydroxyl group, or a hydrogen atom.

Z represents a methylene group, a methine group or an oxygen atom.

$X^5$, $X^6$ and $X^7$ each independently represent a hydrogen atom, a hydroxyl group or an acetoxy group. It is preferred that at most one of $X^5$, $X^6$ and $X^7$ represents a hydroxyl group and the remaining two represent a hydrogen atom. When Z represents a methine group, either $X^5$ or $X^6$ represents a hydrogen atom and the other one does not exist. $X^4$ is preferably a hydrogen atom or a glyceryl group.

$R^8$ and $R^9$ each represent a hydrogen atom, a hydroxyl group, a hydroxymethyl group or an acetoxymethyl group. $R^8$ preferably represents a hydrogen atom or a hydroxymethyl group, while $R^9$ preferably represents a hydrogen atom.

$R^{10}$ represents a linear, branched or cyclic, saturated or unsaturated $C_{5-60}$ hydrocarbon group which may be substituted by a hydroxyl, carboxy or amino group and may have an ether bond, ester bond or amide bond in its main chain. $R^{10}$ preferably represents a linear, branched or cyclic, saturated or unsaturated $C_{5-35}$ hydrocarbon group which may be substituted by a hydroxyl or amino group, or the above-described hydrocarbon group having, to the ω position thereof, a linear, branched or cyclic, saturated or unsaturated $C_{8-22}$ fatty acid, which may be substituted by a hydroxyl group, ester-bound or amide-bound. As the fatty acid to be bound, isostearic acid, 12-hydroxystearic acid or linoleic acid is preferred.

$R^{11}$ represents a hydrogen atom, or a linear or branched, saturated or unsaturated hydrocarbon group having 1 to 30 carbon atoms in total and optionally having a substituent selected from hydroxyl, hydroxyalkoxy, alkoxy and acetoxy groups. When $R^7$ represents a hydrogen atom and Z represents an oxygen atom, $R^{11}$ is a hydrocarbon group having 10 to 30 carbon atoms in total. When $R^7$ represents a hydrocarbon group, $R^{11}$ represents a hydrocarbon group having 1 to 8 carbon atoms in total. Of these, a hydrogen atom and hydrocarbon groups which have 1 to 8 carbon atoms in total and may have 1 to 3 substituents selected from hydroxyl, hydroxyalkoxy and alkoxy groups are preferred. As the hydroxyalkoxy and alkoxy groups, those having 1 to 7 carbon atoms are preferred.

As the ceramide represented by formula (2), those represented by the following formula (5) or (6) are preferred.
(I) Natural or natural type ceramide, or derivative thereof represented by formula (5) (which will hereinafter be called "natural type ceramide")

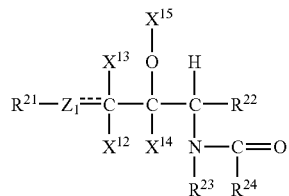

(5)

(wherein, $R^{21}$ represents a linear, branched or cyclic, saturated or unsaturated $C_{7-19}$ hydrocarbon group which may be substituted by a hydroxyl group; $Z_1$ represents a methylene or methine group; $X^{12}$, $X^{13}$ and $X^{14}$ each independently represent a hydrogen atom, a hydroxyl group or an acetoxy group; $X^{15}$ represents a hydrogen atom, or forms an oxo group together with the adjacent oxygen atom (with the proviso that when $Z_1$ represents a methine group, either $X^{12}$ or $X^{13}$ represents a hydrogen atom and the other one does not exist, and when $X^{15}$ represents an oxo group, $X^{14}$ does not exist); $R^{22}$ represents a hydroxymethyl or acetoxymethyl group; $R^{23}$ represents a hydrogen atom or a $C_{1-4}$ alkyl group; $R^{24}$ represents a linear, branched or cyclic, saturated or unsaturated $C_{5-30}$ hydrocarbon group which may be substituted by a hydroxyl group, or the above-described hydrocarbon group having, to the ω position thereof, a linear or branched, saturated or unsaturated $C_{8-22}$ fatty acid, which may be substituted by a hydroxyl group, ester-bound; and a dashed line indicates a possible unsaturated bond).

Preferred are compounds having as $R^{21}$ a linear $C_{7-19}$, more preferably $C_{13-15}$ alkyl group, and as $R^{24}$ a linear $C_{9-27}$ alkyl group which may be substituted by a hydroxyl group or a linear $C_{9-27}$ alkyl group having linoleic acid ester-bound thereto. $X^{15}$ preferably represents a hydrogen atom or forms an oxo group, together with an oxygen atom. As $R^{24}$, a tricosyl group, a 1-hydroxypentadecyl group, a 1-hydroxytricosyl group, a heptadecyl group, a 1-hydroxyundecyl group or a nonacosyl group having linoleic acid ester-bound to the ω position thereof is preferred.

Specific examples of the natural type ceramides include Ceramide Types 1 to 7 obtained by amidation of sphingosine, dihydrosphingosine, phytosphingosine or sphingadienine (for example, FIG. 2 of J. Lipid Res., 24: 759 (1983), and pig and human ceramides as described in FIG. 4 of J. Lipid Res., 35: 2069 (1994)).

The N-alkyl derivatives (for example, N-methyl derivative) of these ceramides are also included.

As these ceramides, natural (D(-) form) optically active derivatives, unnatural (L(+) form) optically active derivatives or a mixture thereof may be used. The relative configuration of these compounds may be any one of the configuration of a natural form, that of an unnatural form and that of their mixture. More preferred ones are compounds such as CERAMIDE 1, CERAMIDE 2, CERAMIDE 3, CERAMIDE 5, and CERAMIDE 6II (listed in INCI, 8th Edition) and those represented by the following formulas.

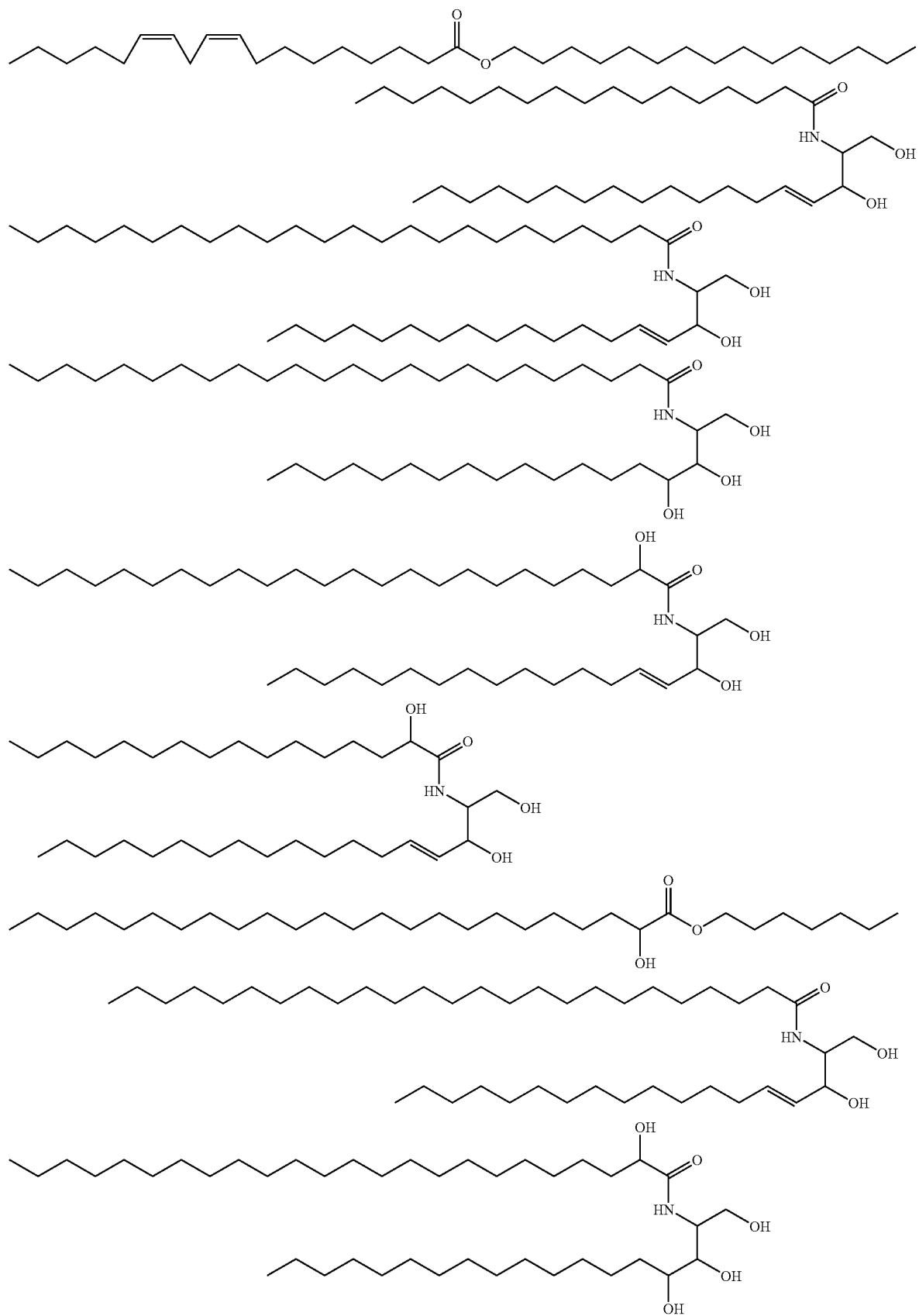

They may be either compounds extracted from natural ceramides or synthesized ones thereof. Commercially available ones can also be used.

Examples of the commercially available natural type ceramides include Ceramide I, Ceramide III, Ceramide IIIA, Ceramide IIIB, Ceramide IIIC, and Ceramide VI (each, product of Cosmo Ferm), Ceramide TIC-001 (product of Takasago International Corp.), CERAMIDE II (product of Quest International), DS-Ceramide VI, DS-CLA-Phytoceramide, C6-Phytoceramide and DS-ceramide Y3S (product of DOOSAN), and CERAMIDE 2 (product of Sederma.

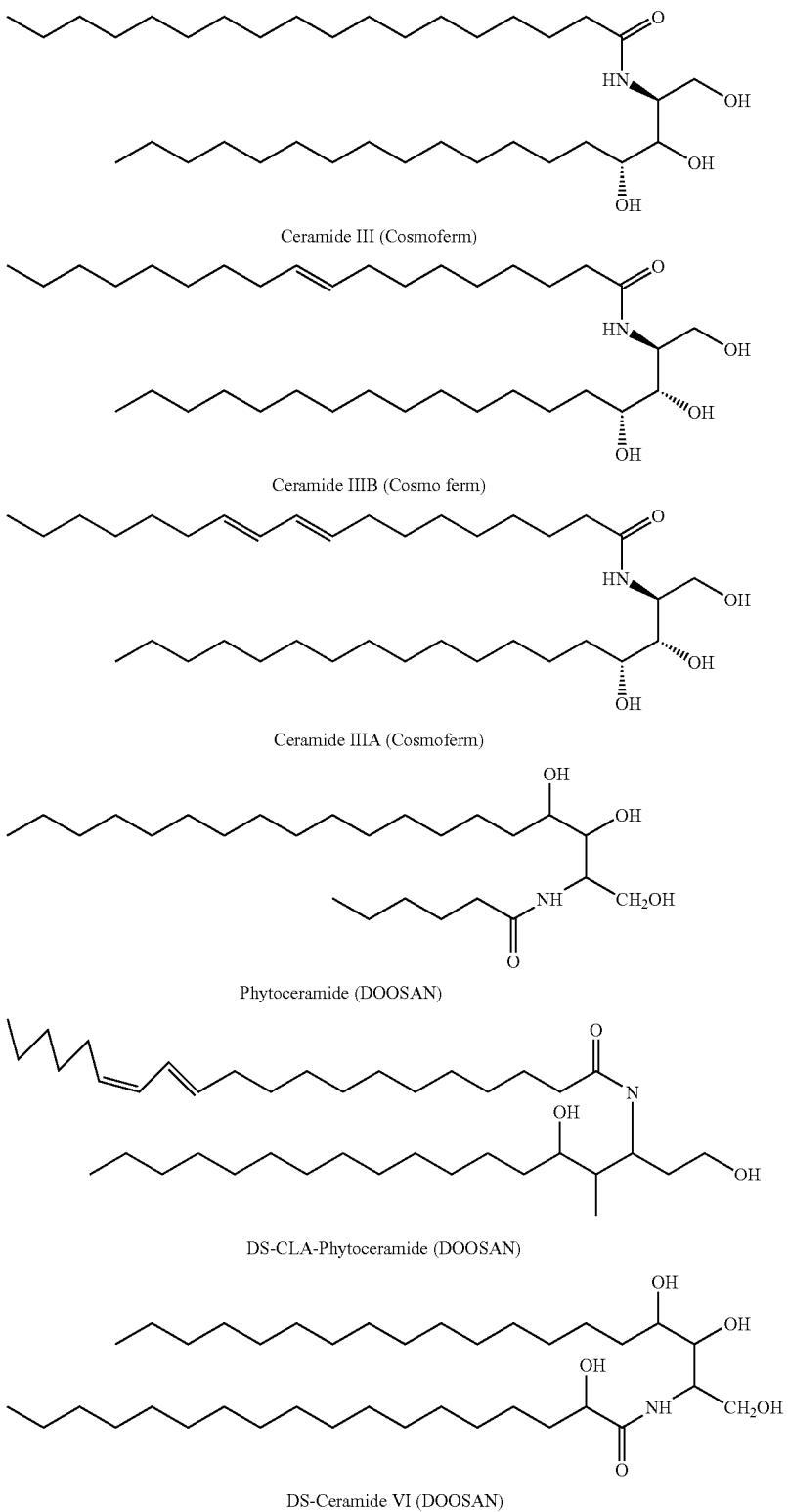

Ceramide III (Cosmoferm)

Ceramide IIIB (Cosmo ferm)

Ceramide IIIA (Cosmoferm)

Phytoceramide (DOOSAN)

DS-CLA-Phytoceramide (DOOSAN)

DS-Ceramide VI (DOOSAN)

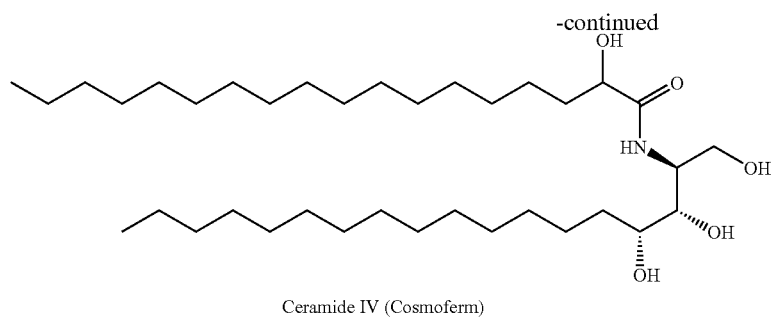

Ceramide IV (Cosmoferm)

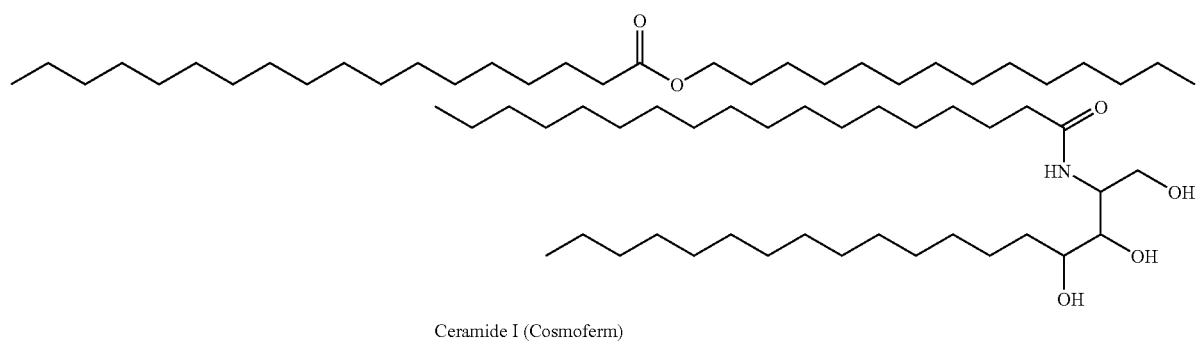

Ceramide I (Cosmoferm)

(II) Pseudo type ceramides represented by the following formula (6)

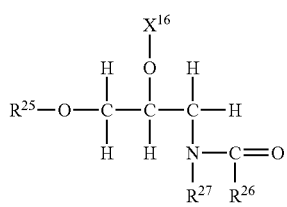

(wherein, $R^{25}$ represents a linear, branched or cyclic, saturated or unsaturated $C_{10-22}$ hydrocarbon group which may be substituted by a hydroxyl group, or a hydrogen atom; $X^{16}$ represents a hydrogen atom, an acetyl group or a glyceryl group; $R^{26}$ represents a linear, branched or cyclic, saturated or unsaturated $C_{5-22}$ hydrocarbon group which may be substituted by a hydroxyl or amino group, or the above-described hydrocarbon group having, to the ω position thereof, a linear or branched, saturated or unsaturated $C_{8-22}$ fatty acid, which may be substituted by a hydroxyl group, ester-bound; and $R^{27}$ represents a hydrogen atom or an alkyl group which has 1 to 30 carbon atoms in total and may have been substituted by a hydroxyl, hydroxyalkoxy, alkoxy or acetoxy group).

Preferred as $R^{26}$ are a nonyl group, a tridecyl group, a pentadecyl group, an undecyl group having linoleic acid ester-bound to the ω position thereof, a pentadecyl group having linoleic acid ester-bound to the ω position thereof, a pentadecyl group having 12-hydroxystearic acid ester-bound to the ω position thereof, and an undecyl group having methyl-branched isostearic acid amide-bound to the ω position thereof.

$R^{27}$ is preferably an alkyl group which has 10 to 30, preferably 12 to 20 carbon atoms in total, and may be substituted by a hydroxyl, hydroxyalkoxy, alkoxy or acetoxy group when $R^{25}$ represents a hydrogen atom; or a hydrogen atom or an alkyl group which has 1 to 8 carbon atoms in total and may be substituted by a hydroxyl, hydroxyalkoxy, alkoxy or acetoxy group when $R^{25}$ represents a linear, branched or cyclic, saturated or unsaturated $C_{10-22}$ hydrocarbon group which may be substituted by a hydroxyl group. The hydroxyalkoxy or alkoxy group as $R^{27}$ preferably has 1 to 7 carbon atoms.

As the pseudo type ceramide of formula (6), those having as $R^{25}$ a hexadecyl group, as $X^{16}$ a hydrogen atom, as $R^{26}$ a pentadecyl group, and as $R^{27}$ a hydroxyethyl group; those having as $R^{25}$ a hexadecyl group, as $X^{16}$ a hydrogen atom, as $R^{26}$ a nonyl group, and as $R^{27}$ a hydroxyethyl group; or those having as $R^{25}$ a hexadecyl group, as $X^{16}$ a glyceryl group, as $R^{26}$ a tridecyl group, and as $R^{27}$ a 3-methoxypropyl group are preferred, with those of formula (6) having as $R^{25}$ a hexadecyl group, as $X^4$ a hydrogen atom, as $R^{26}$ a pentadecyl group, and as $R^{27}$ a hydroxyethyl group being more preferred.

The ceramide of formula (5) is preferably used in combination with the compound of formula (3) serving as Component (A), while the ceramide of formula (6) is preferably used in combination with the compound of formula (4) serving as Component (A). As the compound of formula (1), use of the compound obtained by replacing $COR^{10}$ of the compound of formula (2) bound to the nitrogen atom with H is preferred from the viewpoints of stability and effects.

As Component (C), two or more of these ceramides may be used in combination. The content of Component (C) in the cosmetic composition of the present invention is preferably from 0.001 to 20 weight %, more preferably from 0.01 to 15 weight %, still more preferably from 0.1 to 10 weight %.

In the oil-in-water emulsified cosmetic composition of the present invention, a content ratio of Components (A) and (B) to Component (C) ((A)+(B)/(C)) in terms of weight % is preferably 0.0001 or greater, more preferably from 0.001 to 10, still more preferably from 0.01 to 6 from the viewpoint of stability with the passage of time.

In the present invention, cholesterol, which is, like a ceramide, one of intercellular lipids, and derivatives thereof, higher alcohols having 10 to 50 carbon atoms in total, and higher fatty acids having 10 to 50 carbon atoms in total can also be embraced in oil components emulsifiable by a sphingosine salt other than the ceramide. From the viewpoint of compatibility with the ceramide, these oil components are preferably emulsified, together with the ceramide, by a sphingosine salt.

Examples of the cholesterol derivatives include cholesterol sulfate, isostearyl cholesteryl ester, dihydrocholesterol, cholesteryl stearate, dehydrocholesterol, cholesteryl hydroxystearate, phytosterol and the like.

As the higher alcohol, those having 9 to 25 carbon atoms in total are preferred and examples thereof include stearyl alcohol, cetyl alcohol, isostearyl alcohol, lanolin alcohol acetate, polyoxyethylene lanolin alcohol acetate, hydrogenated lanolin alcohol, cetostearyl alcohol, batyl alcohol lanolin alcohol and the like.

As the higher fatty acid, those having 8 to 30 carbon atoms in total, preferably 10 to 22 carbon atoms in total are preferred. Examples thereof include stearic acid, palmitic acid myristic acid and the like.

Of these, stearyl alcohol, cetyl alcohol, batyl alcohol, cholesterol, stearic acid, palmitic acid and myristic acid are preferred.

The oil component used as Component (D) in the present invention, which is selected from polar oils and hydrocarbon oils, is a component to be emulsified by surfactant (E) as described later.

Examples of the polar oil include fatty acid esters such as diisostearyl malate, octyldodecyl lactate, isotridecyl isononanoate, isopropyl isostearate, and octyldodecyl myristate; ester oils composed of a fatty acid and an alcohol such as neopentyl glycol dicaprate; synthetic ester oils such as amino acid derivatives; and plant oils such as olive oil and jojoba oil.

Examples of the hydrocarbon oil include synthetic or natural ones in the liquid, semi-solid or solid form at 25° C. The hydrocarbon oils in the liquid form include liquid lanolin, liquid paraffin and squalane; and the hydrocarbon oils in the semi-solid or solid form include petrolatum, lanolin, ceresin, and waxes such as microcrystalline wax and the like.

As Component (D), two or more compounds may be used in combination. The content of Component (D) in the cosmetic composition of the present invention is preferably from 0.001 to 50 weight %, more preferably from 0.01 to 30 weight %, still more preferably from 0.01 to 20 weight %.

The surfactant as Component (E) is used to emulsify the oil components other than the ceramide and is not used substantially for emulsification of the ceramide. Examples of the surfactant include, as well as nonionic surfactants, amphoteric surfactants, anionic surfactants, and cationic surfactants, and polymer surfactants such as hydroxyethyl cellulose, polyvinyl alcohol and alkyl-modified water soluble polymer compounds, for example, alkyl-modified polyacrylic acid and alkyl-modified polysaccharide; and natural surfactants such as saponin.

Of these, nonionic surfactants, cationic surfactants and alkyl-modified water soluble polymer compounds are preferred.

The nonionic surfactants include polyoxyethylene hydrogenated castor oil, polyoxyethylene alkyl ethers, and polyoxyethylene sorbitan fatty acid esters. The cationic surfactants include dimethyldistearylammonium chloride, monoalkyltrimethylammonium chlorides, dialkyldimethylammonium chlorides and the like.

The alkyl-modified water soluble polymers include alkyl (meth)acrylate copolymers, alkyl-modified hydroxyethyl cellulose, and polysaccharide derivatives having both hydrophobic and hydrophilic groups as described in Japanese Patent Application Laid-Open No. Hei 11-12119. The alkyl-modified water soluble polymer compounds are commercially available and examples include alkyl acrylate copolymers such as Aqulin 33 (product of ISP); acrylic acid/alkyl methacrylate copolymers (including cross-linked forms thereof) such as Pemulen TR-1, Pemulen TR-2, Carbopol 1382 and Carbopol ETD2020 (each, product of Noveon INC), and Aqupec HV-501ER (product of Sumitomo Seika Chemicals); and alkyl-modified hydroxyethyl cellulose such as Natrosol Plus 330CS, and Polysurf 67 (each, belonging to Aqualon Group, Hercules Inc.). In the derivatives of a (meth) acrylic acid/alkyl(meth)acrylate copolymer or salts thereof, commercially available products, for example, polyoxyethylene alkyl ether ester copolymers of acrylic acid/methacrylic acid/alkyl acrylate/alkyl methacrylate/methacrylic acid (such as alkyl acrylate/alkyl methacrylate/polyoxyethylene (20) stearyl ether copolymer ("Aqulin 22" (product of ISP)) obtained by having a polyoxyethylene alkyl ether ester-bound to a (meth)acrylic acid/alkyl(meth)acrylate copolymer are included.

As Component (E), two or more compounds may be used in combination. The content of Component (E) in the cosmetic composition of the present invention is preferably from 0.01 to 20 weight %, more preferably from 0.01 to 5 weight %, and still more preferably from 0.01 to 3 weight %.

The amount of water contained in the oil-in-water emulsified cosmetic composition of the present invention, that is, the total amount of water used for emulsification of the ceramide and water used for emulsification of the polar oil and hydrocarbon oil is preferably from 5 to 99.9 weight %, more preferably from 30 to 99.9 weight % in the whole composition.

Oil components other than Components (C) and (D) may be incorporated in the oil-in-water emulsified cosmetic composition of the present invention. Such oil components are emulsified substantially by either a sphingosine salt or surfactant serving as an emulsifier. They are preferably selected in consideration of the compatibility with the above-described oil component emulsified by each emulsifier.

As such an oil component, substances ordinarily employed for cosmetic compositions other than the above-described substances, that is, synthetic or natural oil components in the liquid, semi-solid or solid form can be incorporated.

Examples of the oil component in the liquid form include silicone oils such as dimethylpolysiloxane, dimethylcyclopolysiloxane, methylphenyl polysiloxane, methylhydrogen polysiloxane, and higher alcohol modified organopolysiloxane; and fluorine oils such as fluoropolyether and perfluoroalkyl ether silicone.

Examples of the oil component in the semi-solid or solid form include alkyl glyceryl ethers such as glycerin monostearyl ether, glycerin monocetyl ether and the like; and waxes such as carnauba wax, candelilla wax and the like.

In the oil-in-water emulsified cosmetic composition of the present invention, it is possible to incorporate any other component commonly employed for cosmetic compositions, for example, a humectant such as glycine betaine, urea or amino acid and the like; a water soluble thickener such xanthan gum, hydroxyethyl cellulose, methyl cellulose or hydroxypropyl guar gum and the like; a medicinal component such as allantoin or tocopherol acetate and the like; an organic powder such as cellulose powder, nylon powder, crosslinked silicone powder, crosslinked methylpolysiloxane, porous cellulose powder, or porous nylon powder and the like; an inorganic powder such as silica anhydride, zinc oxide or titanium oxide and the like; a cool-feeling imparting agent such as menthol or camphor; pH buffer, antioxidant, ultraviolet absorber, antiseptic, perfume, bactericide or colorant.

The oil-in-water emulsified cosmetic composition of the present invention can be prepared by mixing an emulsion obtained by emulsifying (C) the ceramide with a salt composed of (A) the sphingosine and (B) the acid compound and another emulsion obtained by emulsifying (D) the oil component selected from the polar oils and hydrocarbon oils with (E) the surfactant.

For example, a ceramide emulsion is obtained by dissolving (A) the sphingosine, (B) the acid compound selected from inorganic acids and organic acids having not greater than 5 carbon atoms, and (C) the ceramide under heat at a temperature permitting dissolution; adding about 10 weight % of water to the solution, and then stirring the mixture with a propeller or the like (using a homomixer if necessary).

An OW emulsion is, on the other hand, preferably obtained by stirring (D) the oil component selected from polar oils and hydrocarbon oils, (E) the surfactant and remaining water by using a propeller (using a homomixer if necessary). The oil-in-water emulsified cosmetic composition is then obtained as a final product by mixing the ceramide emulsion with the OW emulsion and stirring.

When a component other than components (A) to (E) is used, it is, if it is anionic, preferably added at the temperature below the melting point of the ceramide emulsion. A water soluble component may be added at any stage during preparation of the ceramide emulsion or the OW emulsion, or even after they are mixed.

It is possible to suppress crystallization of the ceramide and therefore attain a stable emulsified state by emulsifying the ceramide and the other oil component separately and mixing these emulsions thus obtained.

The oil-in-water emulsified cosmetic composition of the present invention is suited for use as a cosmetic lotion, cosmetic emulsion, essence, UV protective cosmetic composition, makeup base, foundation, or makeup cosmetic composition.

EXAMPLES

Examples 1 to 4, Comparative Examples 1 and 2

The oil-in-water emulsified cosmetic compositions having the compositions as shown in Table 1 were prepared by the process described below. The storage stability of each of the cosmetic compositions thus obtained was evaluated. The results are shown collectively in Table 1.

(Preparation Process)

Components (A) to (C) are dissolved under heat at from 80 to 90° C., followed by the addition of 10 weight % of water. The resulting mixture is stirred with a propeller or the like to obtain a ceramide emulsion. Components (D) and (E), remaining water and the other components are stirred with a propeller to obtain an OW emulsion. The ceramide emulsion and the OW emulsion are mixed while stirring, whereby an oil-in-water emulsified cosmetic composition is obtained.

(Evaluation Method)

(1) Storage Stability:

A 50-mL glass bottle is filled with each oil-in-water emulsified cosmetic composition and allowed to stand for one month under three conditions at 50° C., room temperature (25° C.) and −5° C. The appearance is observed visually and evaluated based on the following criteria.

A: Neither emulsion separation nor crystal precipitation is observed.

B: Slight emulsion separation or crystal precipitation is observed.

C: Emulsion separation or crystal precipitation is observed.

TABLE 1

| | Component (Weight %) | Example | | | | Comp. Ex. | |
| --- | --- | --- | --- | --- | --- | --- | --- |
| | | 1 | 2 | 3 | 4 | 1 | 2 |
| A | (1) Phytosphingosine (Cosmo Ferm) | 0.1 | | | | 0.1 | 0.1 |
| | (2) Sphingosine | | | | 0.1 | | |
| | (3) Pseudo type sphingosine (ii) | | 0.2 | 0.2 | 0.1 | | |
| B | (4) Succinic acid | 0.1 | | 0.1 | 0.1 | 0.1 | |
| | (5) L-glutamic acid | | 0.2 | | | | |
| C | (6) Pseudo type ceramide *1 | 1.0 | | | 0.3 | 1.0 | 1.0 |
| | (7) Ceramide type 2 (Sederma) | | 1.0 | 0.5 | | | |
| D | (8) Squalane | 1.0 | 1.0 | | | 1.0 | 1.0 |
| | (9) Olive oil | | 3.0 | 1.0 | 1.0 | | |
| | (10) Petrolatum | | | 2.0 | 2.0 | | |
| E | (11) Polyoxyethylene (25) octyldodecyl ether | 2.0 | | 1.5 | 1.5 | | 2.0 |
| | (12) Polyoxyethylene (60) hydrogenated castor oil | | 2.0 | 1.0 | 1.0 | | |
| | (13) Antiseptic | 0.2 | 0.2 | 0.2 | 0.2 | | |
| | (14) Purified water | Balance | Balance | Balance | Balance | Balance | Balance |
| Total | | 100 | 100 | 100 | 100 | 100 | 100 |
| Stability: | 50° C. | A | A | A | A | C | C |
| | 25° C. | A | A | A | A | C | C |
| | −5° C. | A | A | A | A | C | C |

*1: Compound of the formula (6) in which $R^{25}$ is a hexadecyl group, $X^{16}$ is a hydrogen atom, $R^{26}$ is a nonyl group and $R^{27}$ is a hydroxyethyl group.

All the oil-in-water emulsified cosmetic compositions obtained in Examples 1 to 4 had an excellent storage stability and a good feeling upon use. The cosmetic composition of Comparative Example 1 not containing (E) the surfactant and the composition of Comparative Example 2 not containing (B) the acid compound were inferior in stability of the emulsion.

Example 5

Cosmetic Emulsion

The cosmetic emulsion having the composition as shown in Table 2 was prepared by the process described below. The cosmetic emulsion thus obtained was excellent in both emulsion stability and feeling upon use.
(Preparation Process)

Components from (3) to (7), (11) and (13) are dissolved under heat at 90° C. The resulting solution and another solution obtained by dissolving Components (1) and (2) in 5 weight % of water under heat at 90° C. are stirred for 20 minutes with a propeller, stirred in a homomixer (at 7000 rpm), and cooled to 25° C. while stirring with a propeller, whereby a ceramide emulsion is obtained.

In a homomixer (at 7000 rpm), Components from (8) to (10) are dispersed in another solution obtained by dissolving Component (12) in the remaining water, followed by the addition of the ceramide emulsion. They are mixed by stirring to obtain a cosmetic emulsion.

TABLE 2

| | | (Component) | (weight %) |
|---|---|---|---|
| A | 1 | Phytosphingosine | 0.2 |
| B | 2 | L-Glutamic acid | 0.09 |
| C | 3 | Pseudo type ceramide *1 | 2.0 |
| | 4 | Stearic acid | 0.42 |
| | 5 | Palmitic acid | 0.3 |
| | 6 | Cholesteryl isostearate | 0.36 |
| | 7 | Cholesterol | 0.55 |
| D | 8 | Squalane | 5.0 |
| | 9 | Olive oil | 10.0 |
| | 10 | L-Arginine | 0.07 |
| | 11 | 86% Glycerin | 10.0 |
| E | 12 | Sulfostearyl polysaccharide *2 | 0.5 |
| | 13 | Methylparaben | 0.2 |
| | 14 | Purified water | Balance |
| | | Total | 100 |

*2: Sodium hydroxyethylcellulose hydroxypropyl stearyl ether hydroxypropylsulfonate (Kao)

Example 6

Cosmetic Lotion

A cosmetic lotion having the composition as shown in Table 3 was prepared by the process described below. This cosmetic lotion was excellent in both emulsion stability and feeling upon use.
(Preparation Process)

Components (1), (3), (7) and a portion (about 3 weight %) of Component (6) are dissolved under heat at from 80 to 90° C. To the resulting solution, another solution obtained by dissolving Component (2) and a portion (about 6 weight %) of water under heat at 80° C. is added in portions while stirring with a propeller and the reaction mixture is retained for 20 minutes. After addition of water (about 50 weight %) heated to about 80° C., the mixture is cooled to 25° C. while stirring with a propeller, whereby a ceramide emulsion is obtained.

Components (4) and (5) and the remaining portion of Component (6) are dissolved under heat at from 80 to 90° C. While stirring with a propeller, the remaining water is added in portions to the resulting solution. After cooling to 25° C., the ceramide emulsion is added, followed by mixing while stirring, whereby a cosmetic lotion is obtained.

TABLE 3

| | | (Component) | (weight %) |
|---|---|---|---|
| A | 1 | Phytosphigosine | 0.2 |
| B | 2 | L-Glutamic acid | 0.12 |
| C | 3 | Pseudo type ceramide *2 | 0.5 |
| D | 4 | Isotridecyl isononanoate | 0.02 |
| E | 5 | Polyoxyethylene (60) hydrogenated castor oil | 0.5 |
| | 6 | 86% Glycerin | 10.0 |
| | 7 | Methylparaben | 0.2 |
| | 8 | Purified water | Balance |
| | | Total | 100 |

Example 7

Cosmetic Emulsion

The cosmetic emulsion having the composition as shown in Table 4 was prepared by the process described below. The cosmetic emulsion thus obtained was excellent in both emulsion stability and feeling upon use.
(Preparation Process)

Components from (3) to (7), (11) and (13) shown in Table 4 are dissolved under heat at 90° C. The resulting solution and another solution obtained by dissolving Components (1) and (2) in a portion (about 5 weight %) of water under heat at 90° C. are stirred with a propeller for 20 minutes, stirred in a homomixer (at 7000 rpm) and cooled to 25° C. while stirring with a propeller, whereby a ceramide emulsion is obtained.

In a solution obtained by dissolving Component (12) in the remaining water, Components (8) to (10) are dispersed using a homomixer (at 7000 rpm), followed by the addition of the ceramide emulsion. They are mixed while stirring to obtain a cosmetic emulsion.

TABLE 4

| | | (Component) | (weight %) |
|---|---|---|---|
| A | 1 | Pseudo type sphingosine | 0.2 |
| B | 2 | L-Glutamic acid | 0.09 |
| C | 3 | Pseudo type ceramide *1 | 2.0 |
| | 4 | Stearic acid | 0.42 |
| | 5 | Palmitic acid | 0.3 |
| | 6 | Cholesteryl isostearate | 0.36 |
| | 7 | Cholesterol | 0.55 |
| D | 8 | Squalane | 5.0 |
| | 9 | Olive oil | 10.0 |
| | 10 | L-Arginine | 0.07 |
| | 11 | 86% Glycerin | 10.0 |
| E | 12 | Cetyl hydroxyethyl cellulose | 0.5 |
| | 13 | Methylparaben | 0.2 |
| | 14 | Purified water | Balance |
| | | Total | 100 |

The oil-in-water emulsified cosmetic composition of the present invention stably contains oil components including a ceramide and the like, and has excellent storage stability.

The invention claimed is:

1. A process for preparing an oil-in-water emulsified cosmetic composition, comprising:

Mixing a first emulsion and a second emulsion:
wherein:
the first emulsion is obtained by mixing: (A) a sphingosine, (B) an acid compound, (C) a ceramide, and water, the sphingosine (A) and the acid compound (B) forming a salt of the sphingosine;
this second emulsion is obtained by mixing: (D) an oil component, (E) a surfactant, and water;
a molar ratio of the acid compound (B) to the sphingosine (A) ((B):(A)) is from 0.5 to 3;
a weight ratio of the sphingosine (A) and the acid compound (B) to the ceramide (C) in the composition (((A)+(B)):(C)) is from 0.01 to 6;
the sphingosine (A) is present in an amount of 0.01 to 1.5% by weight relative to a total weight of the composition;
the acid compound (B) is present in an amount of 0.01 to 1.5% by weight relative to a total weight of the composition;
the ceramide (C) is present in an amount of 0.1 to 10% by weight relative to a total weight of the composition;
the oil component (D) is present in an amount of 0.01 to 20% by weight relative to a total weight of the composition;
the surfactant (E) is present in an amount of 0.01 to 3% by weight relative to a total weight of the composition;
the sphingosine (A) comprises at least one member selected from the group consisting of phytosphingosine, sphingosine, and a pseudo-type sphingosine according to the following formula

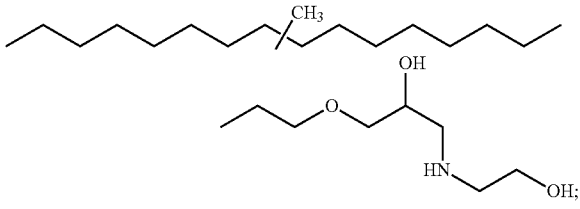

the acid compound (B) comprises at least one member selected from the group consisting of phosphoric acid, succinic acid, citric acid, lactic acid, glutamic acid, and aspartic acid;
the ceramide (C) comprises at least one member selected from the group consisting of ceramide 1, ceramide 2, ceramide 3, ceramide 5, ceramide 6II, and a pseudo-type ceramide represented by formula (6):

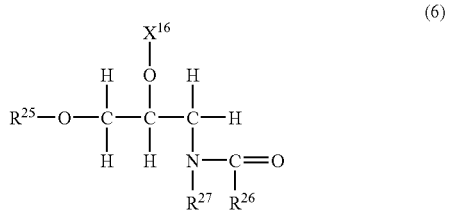

(6)

where $R^{25}$ is a hexadecyl group, $X^{16}$ is a hydrogen atom, $R^{26}$ is a nonyl group, and $R^{27}$ is a hydroxyethyl group;

the oil component (D) is selected from polar oils and hydrocarbon oils; and the first emulsion is free of surfactants other than a salt of the sphingosine (A).

2. The process of claim 1, wherein the first emulsion is obtained by adding a mixture of the acid compound (B) and water to a mixture of the sphingosine (A) and the ceramide (C).

3. The process of claim 1, wherein the first emulsion is obtained by mixing a mixture of the sphingosine (A), the acid compound (B) and the ceramide (C) with water.

4. The process of claim 1, wherein the sphingosine (A) is cationized.

5. The process of claim 1, wherein the surfactant (E) comprises at least one nonionic surfactant selected from the group consisting of a polyoxyethylene hydrogenated castor oil, a polyoxyethylene alkyl ether and a polyoxyethylene sorbitan fatty acid ester.

6. The process of claim 1, wherein the surfactant (E) comprises at least one polymer surfactant selected from the group consisting of a hydroxyethyl cellulose, a polyvinyl alcohol and an alkyl-modified water soluble polymer compound.

7. The process of claim 6, wherein the polymer surfactant comprises at least one alkyl-modified water soluble polymer selected from the group consisting of an alkyl-modified polyacrylic acid, an alkyl-modified polysaccharide, an alkyl (meth)acrylate copolymer, an alkyl-modified hydroxyethyl cellulose and a polysaccharide derivative having both hydrophobic and hydrophilic groups.

8. The process of claim 1, wherein the surfactant (E) is sodium hydroxyethylcellulose hydroxypropyl stearyl ether hydroxypropyl sulfate.

9. The process of claim 1, wherein the surfactant (E) is cetyl hydroxyethyl cellulose.

10. The process of claim 1, wherein the second emulsion is free of ceramides.

11. The process of claim 1, wherein the surfactant (E) comprises a surfactant selected from the group consisting of nonionic surfactants, cationic surfactants, and alkyl-modified water soluble polymer compounds.

12. The process of claim 1, wherein mixing the first emulsion and the second emulsion comprises:
dissolving the sphingosine (A), the acid compound (B) and the ceramide (C) together while applying heat to obtain a first mixture;
cooling the first mixture;
dissolving the oil component (D) and the surfactant (E) while applying heat to obtain a second mixture;
cooling the second mixture; and
combining the first mixture and the second mixture after cooling.

13. The process of claim 1, wherein the sphingosine (A) comprises phytosphingosine.

14. The process of claim 1, wherein the sphingosine (A) comprises sphingosine.

15. The process of claim 1, wherein the sphingosine (A) comprises the pseudo-type sphingosine according to the formula

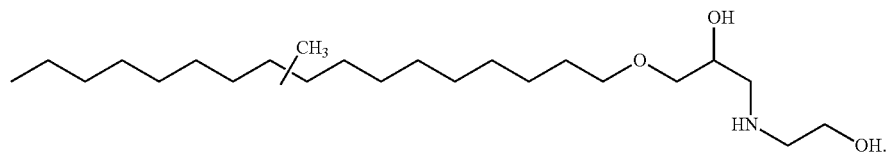

16. The process of claim 1, wherein the ceramide (C) comprises the ceramide (C) comprises at least one member selected from the group consisting of ceramide 1, ceramide 2, ceramide 3, ceramide 5, and ceramide 6II.

17. The process of claim 1, wherein the ceramide (C) comprises the pseudo-type ceramide represented by represented by formula (6):

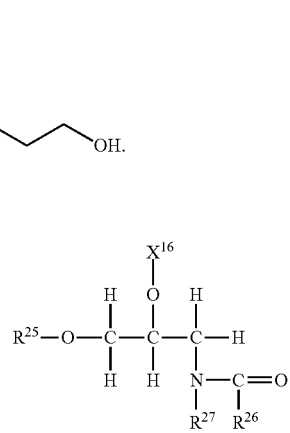

where $R^{25}$ is a hexadecyl group, $X^{16}$ is a hydrogen atom, $R^{26}$ is a nonyl group, and $R^{27}$ is a hydroxyethyl group.

* * * * *